United States Patent

El Gazayerli

Patent Number: 5,257,637
Date of Patent: Nov. 2, 1993

[54] METHOD FOR SUTURE KNOT PLACEMENT AND TYING

[76] Inventor: Mohamed M. El Gazayerli, 476 Steeple Chase, Bloomfield Hills, Mich. 48013

[21] Appl. No.: 952,131

[22] Filed: Sep. 28, 1992

Related U.S. Application Data

[63] Continuation of Ser. No. 673,959, Mar. 22, 1991, abandoned.

[51] Int. Cl.$^5$ ............................................. A61B 17/00
[52] U.S. Cl. ................................... 128/898; 606/139; 606/148; 606/205; 606/207
[58] Field of Search ............... 606/148, 144, 139, 127, 606/128, 205–207; 128/898

[56] References Cited

U.S. PATENT DOCUMENTS

| | | | |
|---|---|---|---|
| 671,337 | 4/1901 | Gibson | 606/148 |
| 1,855,546 | 4/1932 | File | 606/139 |
| 2,316,297 | 4/1943 | Southerland et al. | 128/326 |
| 2,518,994 | 8/1950 | Miller | 606/205 |
| 3,687,138 | 8/1972 | Jarvik | 128/326 |
| 3,871,379 | 3/1975 | Clarke | 606/148 |
| 4,890,615 | 1/1990 | Caspari et al. | 606/146 |
| 4,923,461 | 5/1990 | Caspari et al. | 606/146 |
| 4,957,498 | 9/1990 | Caspari et al. | 606/146 |
| 4,961,741 | 10/1990 | Hayhurst | 606/139 |
| 5,100,421 | 3/1992 | Christoudias | 606/147 |

OTHER PUBLICATIONS

New Product Information Bulletin No. 23-63, Down Bros. and Mayer & Phelps Ltd.
United States Surgical Corporation.

Primary Examiner—Stephen C. Pellegrino
Assistant Examiner—Jeffrey A. Schmidt
Attorney, Agent, or Firm—Flynn, Thiel, Boutell & Tanis

[57] ABSTRACT

An instrument is provided for placing and tightening a knot tied in end lengths of a suture at desired body tissue through an access tube such as a cannula. The instrument includes an elongated member having a distal working end positionable inside the body through the access tube and a proximal end manipulatable outside the body. First and second jaws are disposed at the distal working end so as to be relatively movable (e.g., closeable/openable). Each jaw includes an open-ended, axially extending slot therethrough for receiving a respective one of the free end lengths of the suture extending from body tissue to be sutured as the instrument is advanced in the access tube. Handles operable at the proximal end of the elongated member are provided to relatively move the first and second jaws between closed and an opened positions. The instrument is positioned between the end lengths of the suture after the extracorporal knot is tied with the closed jaws proximate the knot so as to push the knot through the access tube as the instrument is advanced therein to place the working end inside the body. The jaws are then opened inside the body such that the knot is tightened with the opened jaws as they are moved toward the tissue to be sutured.

3 Claims, 2 Drawing Sheets

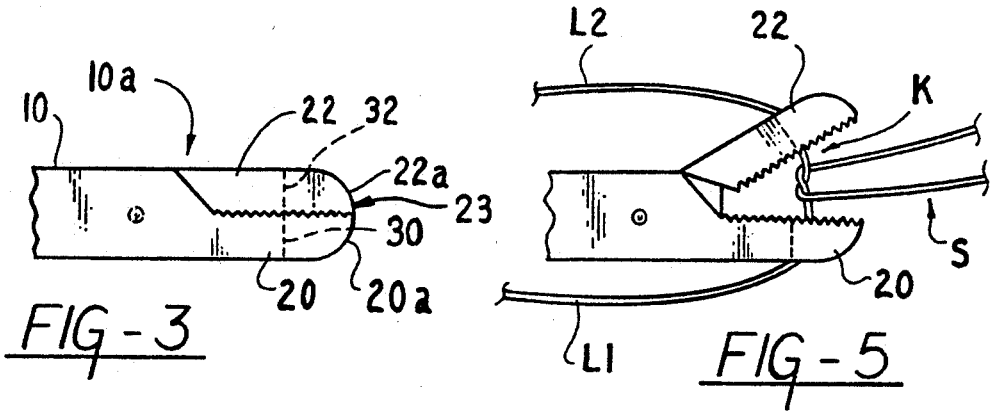
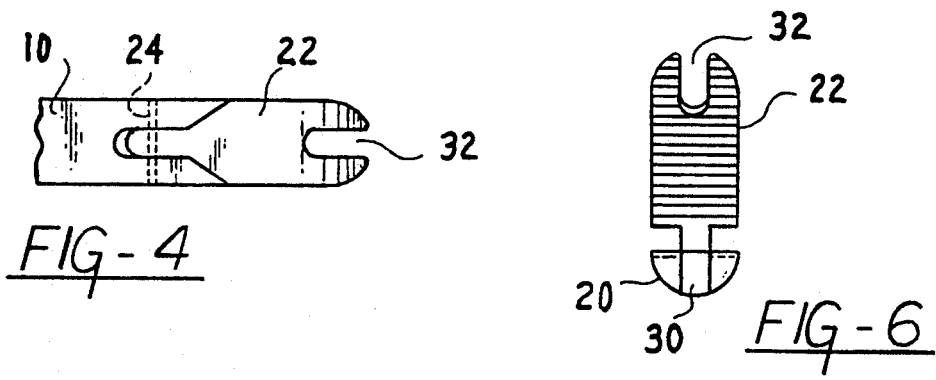
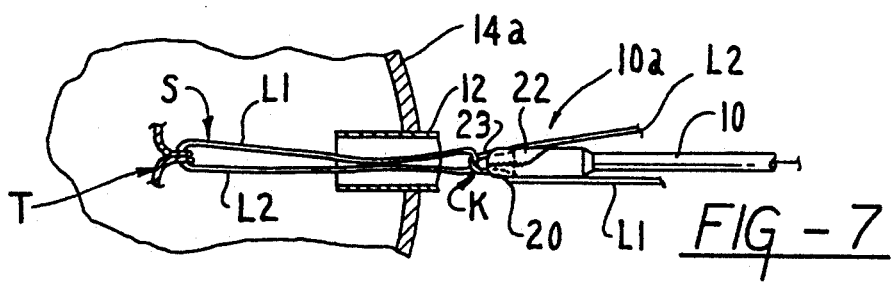
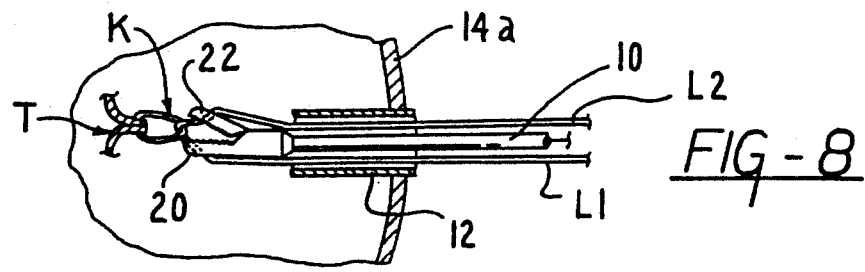
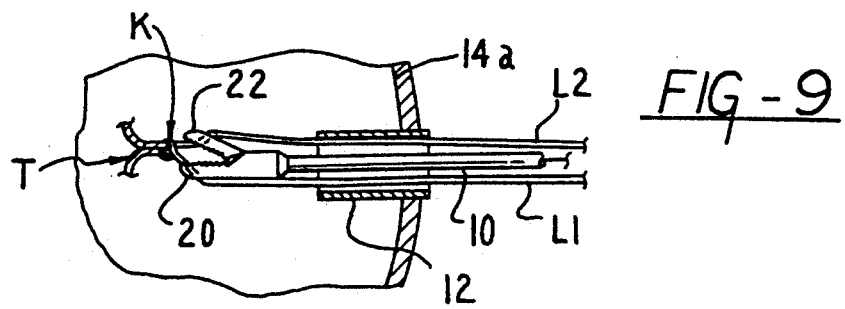

METHOD FOR SUTURE KNOT PLACEMENT AND TYING

This application is a continuation of U.S. Ser. No. 07/673,959, filed Mar. 22, 1991, now abandoned.

FIELD OF THE INVENTION

The present invention relates to a surgical instrument and method and, more particularly, to a knot placing and tightening instrument especially useful in endoscopic surgery.

BACKGROUND OF THE INVENTION

Endoscopic surgery encompasses surgery on various parts of the body requiring only small incisions or portals for insertion of surgical instruments through an access tube (e.g., a cannula) and manipulated externally of the body. Endoscopic surgery is preferable over open surgery to avoid trauma associated with large incisions as well as hospitalization and prolonged recovery periods associated with open surgery. Endoscopic surgery is used whenever possible to achieve the same results as open surgery without the aforementioned disadvantages thereof.

Recently, laparoscopic cholecystectomy has become a popular surgical procedure since it involves the same procedure as an open cholecystectomy (using different surgical instruments) with, however, the benefits of better visualization and less patient morbidity. Hernia repair represents another surgical procedure that could be conducted as an endoscopic procedure rather than an open procedure. However, to date, widespread laparoscopic repair of direct and indirect inguinal hernias has been hampered by the inability to suture through the cannula in an expeditious manner.

The Caspari et al U.S. Pat. Nos. 4,890,615 and 4,923,461 describe an arthroscopic suturing instrument including a pair of relatively movable jaws for clamping tissue while a hollow needle on one of the jaws is actuated to penetrate the tissue and is then received in an aperture in the other of the jaws. A suture feed mechanism is provided to feed suture material through the hollow needle and the aperture. The jaws are then opened, and the instrument withdrawn from the body through a cannula to pull the free end of the suture material out of the body so that the surgeon can tie a suitable extracorporal knot in the suture material. The knot is then moved into the body through the cannula to a position proximate the sutured tissue by a conventional throw stick, and the surgeon tightens the knot by pulling on either or both ends of the suture material remaining outside the body.

The Southerland et al U.S. Pat. No. 2,316,297 disclosures a surgical instrument for facilitating the tying of blood vessels and arteries, particularly in throat operations. The instrument includes a pair of relatively movable jaws operable to clamp an artery after a suture has been loosely tied thereabout. The free ends of the suture are passed through slots in a slidable, jaw-locking barrel, through an eyelet on the barrel, and then secured in a clip on the barrel after the suture is loosely tied. The barrel is then slid over the jaws to lock them in the clamped position. The ends of the suture are then removed from the clip and a steady pull is exerted thereon to cause the knot to tighten around the artery. A short tube mounted on the barrel is manually slid over the barrel to cut the ends of the suture at each side of the tightened knot.

SUMMARY OF THE INVENTION

The present invention provides a surgical instrument, as well as surgical method, for improving suturing in endoscopic surgical procedures by facilitating the placement and tightening of a suture knot at desired body tissue through an access tube in the body.

An instrument of the present invention includes an elongated member having a distal working end positionable inside the body through an access tube (e.g., a cannula) and a proximal end manipulatable outside the body. First and second jaws are disposed at the distal working end so as to be movable relative to one another (e.g., closeable/openable). The jaws are closeable to allow the working end of the instrument to pass through the access tube.

Each jaw includes an opening therethrough for receiving a respective one of the free end lengths of a suture (or ligature) extending from body tissue to be sutured through the access tube. Preferably, each opening comprises an open-ended, elongated slot formed in each jaw at the free end thereof and extending axially therealong. Means operable at the proximal end of the elongated member is provided to relatively move the first and second jaws so as to render them relatively closeable and openable.

In accordance with a method of the invention, the two end lengths of the suture extending from the body tissue are passed through the access tube (e.g., cannula) to the exterior of the body. The end lengths are tied in a suitable extracorporal knot (i.e., exteriorly of the body). The jaws of the surgical instrument are closed and placed between the two end lengths with the closed jaws located proximate the knot to push it through the access tube as the instrument is advanced therein. Each suture end length is received in a respective jaw opening when the jaws are positioned proximate the knot and as the jaws are moved toward the tissue to be sutured. The surgeon holds the free end lengths in one hand and the instrument in another hand. Once inside the body proximate the tissue, the jaws of the instrument are opened. The knot is tightened at the tissue with the jaws opened and with each suture end length received in a respective jaw opening. The opened jaws facilitate placement and tightening of the knot by permitting the surgeon to view the knot through an endoscope during placement/tightening and by permitting correction of any twist in the end lengths of the suture during placement/tightening to provide a square knot, as is usually desired, at the tissue to be sutured. Thereafter, the instrument is withdrawn from the tightened knot, and the jaws are closed to allow the instrument to be removed from inside the body through the access tube. The end lengths of the suture can be cut at the sutured tissue by a separate cutting instrument passed through the access tube.

DESCRIPTION OF THE DRAWINGS

FIG. 3 is an enlarged fragmentary side elevational view of the jaws in the closed position at the working end of the instrument.

FIG. 4 is an enlarged fragmentary plan view of the top jaw in the closed position.

FIG. 5 is an enlarged fragmentary side elevational view of the top jaw opened.

FIG. 6 is an enlarged fragmentary front elevational view of the jaws in the opened position.

FIG. 7 is a schematic sectional view of the patient's body with the instrument of FIG. 1 positioned between the end lengths of the suture after the extracorporal knot is tied and with the closed jaws positioned proximate the knot for pushing it through the access tube as the instrument is advanced therein.

FIG. 8 is a similar view to FIG. 7 after the instrument is advanced in the access tube to position the jaws inside the body and after the jaws are opened.

FIG. 9 is a similar view to FIG. 8 after the instrument is further advanced in the access tube to tighten the knot at the tissue to be sutured.

DETAILED DESCRIPTION OF THE INVENTION

Figure 1:
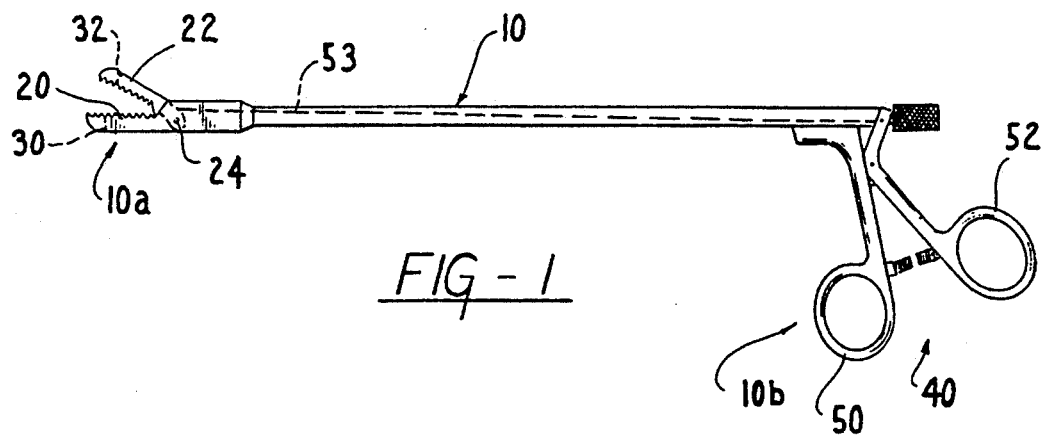
FIG. 1 is an elevational view of a surgical instrument in accordance with one embodiment of the invention.
Figure 2:
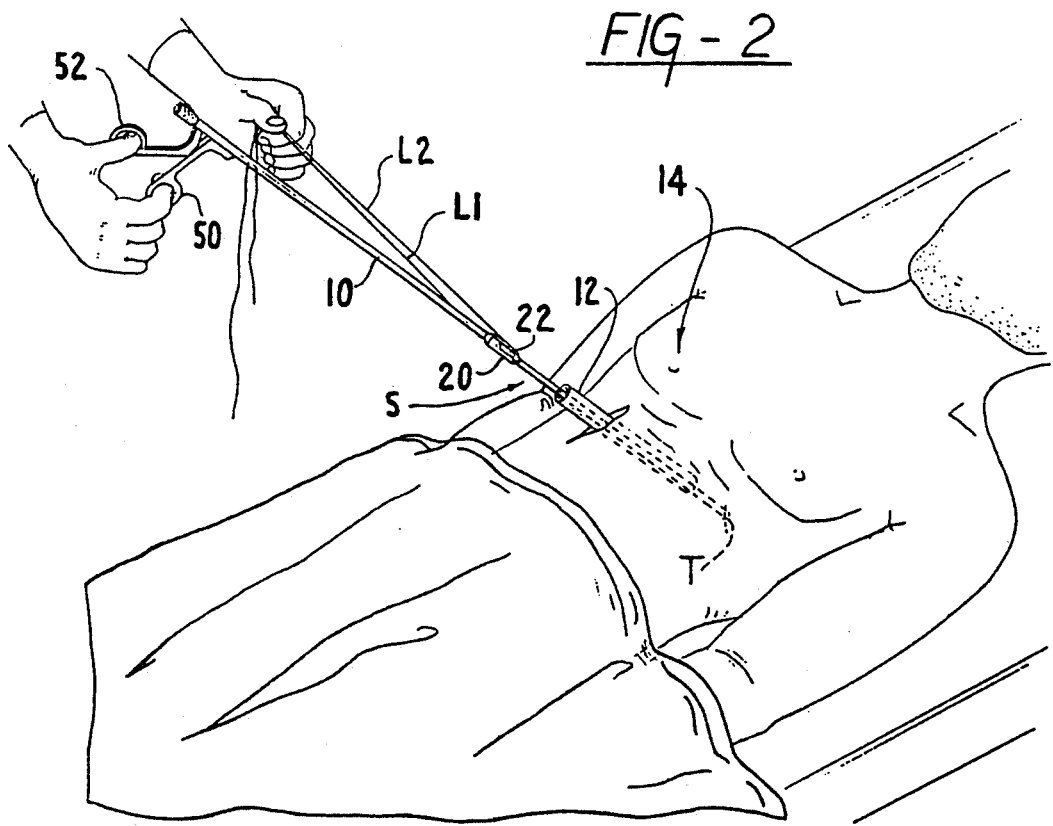
FIG. 2 is a schematic perspective view illustrating the instrument of FIG. 1 ready for insertion in an access tube in a patient's body.

FIGS. 1-6 illustrate one embodiment of an instrument of the invention for placing and tightening an extracorporal suture knot tied in end lengths of a suture (or ligature) at a desired body tissue location through an access tube 12, such as a cannula, inserted in the body fascia 14a. In particular, the instrument includes an elongated member 10, such as an elongated tubular member, adapted to pass through the access tube 12 (see FIGS. 7-9) inserted inside the body 14 of the patient. The elongated member 10 has a distal working end 10a positionable inside the body through the access tube 12 and a proximal end 10b manipulatable outside the body as is apparent from the Figures. First and second axially elongated jaws 20,22 are disposed at the working end 10a of the elongated member 10 so as to be movable relative to one another (e.g., closeable/openable). In the embodiment illustrated in the Figures, the first jaw 20 is fixed or stationary on the elongated member 10 whereas the second jaw 22 is pivotably mounted thereon typically by a pivot pin 24, although it is not so limited. For example, one or both of the jaws 20,22 can be pivotably or otherwise movably mounted on the elongated member 10.

Each jaw 20,22 includes an opening therethrough preferably comprising an open-ended, elongated slot 30,32 formed (e.g., machined) at the free leading end 20a, 22a thereof and extending axially along the length of each jaw. Each slot 30,32 is adapted to receive a respective one of the free end lengths L1,L2 of a suture S extending from body tissue T to be sutured as shown in FIGS. 7-9. In one embodiment of the invention, each jaw 20,22 is about 10 mm (millimeters) in length, about 5 mm in width and about 2.5 mm in thickness. When closed, the jaws 20,22 are of a size capable of passing through the access tube 12 having a minimum inner diameter of 5 mm. Each slot 30,32 is about 4 mm in length and about 2 mm in width although the invention is not limited to these dimensions. The opening in each jaw 20,22 may alternately comprise a cylindrical or other shaped through-hole or aperture to receive the end lengths L1,L2 of the suture.

The instrument also includes means 40 operable at the proximal end 10b of the elongated member 10 to relatively move the first and second jaws 20,22 between a closed position adjacent one another, FIG. 3, and an open position spaced apart from one another, FIGS. 5-6. Such means typically comprises handles 50 and 52.

The handle 50 is fixed relative to the elongated member 10. The handle 52 is operatively connected to the movable (pivotable) jaw 22 by a rod or cable 53 (shown schematically in FIG. 1 by dashed lines). Such a handle actuation mechanism is known and provided on commercially available 5 mm single or double action grasping forceps available from Karl Storz Endoscopy, American Instrument, V. Mueller and U.S. Surgical Corp. The invention is not limited to the particular actuation mechanism described and may be practiced using various jaw actuation mechanisms, such as shown in U.S. Pat. Nos. 4,957,498; 3,687,138 and 2,316,297.

One embodiment of a method of the invention for placing and tightening an extracorporal knot tied in end lengths L1,L2 of the suture S through the access tube 12 involves passing the end lengths L1,L2 of the suture through the access tube 12 to the exterior of the body, FIG. 7, after the suture S is made initially through the tissue T by conventional procedures. A loose surgeon's knots K (one shown) is then tied in the end lengths L1,L2 exteriorly of the body (i.e., an extracorporal knot is made). Typically, a first knot will comprise a double knot for placement and tightening at the tissue T to be sutured. Then, one or more additional knots of the single knot type can be tied and tightened at the tissue T subsequent to tightening of the first knot K as desired by the surgeon.

After the knot K is tied, the relatively movable jaws 20,22 of the surgical instrument are positioned between the two suture end lengths L1,L2 with the jaws 20,22 closed and proximate the knot K so as to push it through the access tube 12 as the working end 10a of the instrument is advanced therein. Each end length L1,L2 is received in a respective open-ended slot 30,32 of the respective jaw 20,22 as the working end is advanced in the access tube 12, e.g., see FIGS. 7-9. The closed jaws 20,22 form a nose 23 that is adapted to push the knot K ahead of it as the working end 10a is advanced in the access tube 12 by the surgeon, FIG. 7.

During advancement of the instrument, the surgeon holds the end lengths L1,L2 in one hand, while the other hand grips the handles 50,52 of the instrument to manipulate it through the access tube 12.

Once the closed jaws 20,22 are inside the body fascia 14a, the jaws are opened by actuation of the handles 50,52, FIG. 8. The working end 10a is advanced further toward the tissue T to be sutured with the jaws 20,22 opened and with the end lengths L1,L2 received in a respective slot 30,32, while the surgeon continues to hold the end lengths L1,L2 of the suture S so that the knot K will be tightened at the tissue T to be sutured, FIG. 9. In this way, an extracorporal suture knot K can be placed and tightened at the desired tissue location inside the body through the access tube 12 in accordance with the invention.

During the procedure described above, the opened jaws 20,22 facilitate knot placement and tightening. For example, any twisting of the end lengths L1,L2 of the suture S can be eliminated inside the body by counter twisting of the instrument so that the surgeon can place a square suture knot (as opposed to a twisted knot) at the tissue T as is usually desired. Moreover, the opened jaws 20,22 enable the surgeon to view the knot K through an endoscope as the knot is tightened and placed at the tissue T. In addition, should the end lengths L1,L2 fall out of the slots 30,32, they can be readily manipulated back into the slots by the surgeon.

As mentioned above, additional extracorporal suture knots can be subsequently made, placed and tightened at the tissue T in the same manner as described above for the knot K with traction maintained.

After the knot K is placed and tightened at the tissue T, the working end 10a of the instrument is moved away from the tissue, and the jaws 20,22 are closed to enable withdrawal of the working end 10a through the access tube 12 to outside the body fascia 14a. Another instrument can then be inserted through the access tube 12 to cut the end lengths L1,L2 at the tightened knot K.

The surgical instrument and method of the present invention are especially useful for laparoscopic hernia repair of direct and indirect inguinal hernias using transversalis fascia and iliopubic tract. The instrument and method of the invention are not limited to hernia repairs, however, and, instead, are useful in other endoscopic surgical procedures where placement and tightening of a suture knot through an access tube is necessary.

While the invention has been described in terms of specific embodiments thereof, it is not intended to be limited thereto but rather only to the extent set forth hereafter in the following claims.

I claim:

1. A method of placing and tightening a knot tied in end lengths of a suture at body tissue through an access tube, comprising:

passing end lengths of a suture from a body tissue through an access tube to the exterior of the body, tying a knot in the end lengths exteriorly of the body, positioning relatively movable jaws of an instrument between the suture end lengths with the jaws in a closed position and proximate the knot so as to push it through the access tube as the jaws are advanced therein with each end length received in a respective opening of a respective jaw, relatively moving the jaws to an open position after they are positioned inside the body, and advancing the opened jaws toward the body tissue with each suture end length received in said respective opening so as to tighten the knot at the tissue.

2. The method of claim 1 including withdrawing the instrument through the access tube with the jaws closed after the knot is tightened.

3. The method of claim 1 wherein each end length is received in an elongated, open-ended slot of a respective jaw as the instrument is advanced in the access tube.

* * * * *